(12) United States Patent
Banerjee et al.

(10) Patent No.: US 11,571,162 B2
(45) Date of Patent: Feb. 7, 2023

(54) RECURRENT NEURAL NETWORK ARCHITECTURE BASED CLASSIFICATION OF ATRIAL FIBRILLATION USING SINGLE LEAD ECG

(71) Applicant: Tata Consultancy Services Limited, Mumbai (IN)

(72) Inventors: Rohan Banerjee, Kolkata (IN); Avik Ghose, Kolkata (IN); Sundeep Khandelwal, Noida (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 479 days.

(21) Appl. No.: 16/827,812

(22) Filed: Mar. 24, 2020

(65) Prior Publication Data

US 2020/0352461 A1 Nov. 12, 2020

(30) Foreign Application Priority Data

May 9, 2019 (IN) .............................. 201921018639

(51) Int. Cl.
*G08B 23/00* (2006.01)
*A61B 5/361* (2021.01)
(Continued)

(52) U.S. Cl.
CPC .............. *A61B 5/361* (2021.01); *A61B 5/352* (2021.01); *A61B 5/366* (2021.01); *G06N 3/0445* (2013.01);
(Continued)

(58) Field of Classification Search
CPC ......... A61B 5/361; A61B 5/352; A61B 5/366; A61B 5/364; A61B 5/7264; G06N 3/0445;
(Continued)

(56) References Cited

U.S. PATENT DOCUMENTS 8,560,058 B2 10/2013 Babaeizadeh et al.
9,486,155 B2 * 11/2016 Sarkar .................. A61N 1/3987
(Continued)

FOREIGN PATENT DOCUMENTS

WO WO-2008/007236 1/2008

OTHER PUBLICATIONS

Chang, Y-C. et al. "AF Detection by Exploiting the Spectral and Temporal Characteristics of ECG Signals with the LSTM Model," *2018 Computing in Cardiology Conference (CinC)*, Sep. 23-26, 2018, Maastricht, The Netherlands; 4 pages.
(Continued)

*Primary Examiner* — Anh V La
(74) *Attorney, Agent, or Firm* — Finnegan, Henderson, Farabow, Garrett & Dunner LLP (57) ABSTRACT

Conventionally, Atrial Fibrillation (AF) has been detected using atrial analyses which is vulnerable to background noise. Again there is a dependency on statistical features which are extracted from R-R intervals of long ECG recordings. The present disclosure addresses AF detection from single lead short ECG recordings of less than one minute wherein automatic detection of P-R and P-Q intervals is difficult, which introduces error in feature computing from the segregated intervals and compromises the performance of the classifier. In the present disclosure, a Recurrent Neural Network (RNN) based architecture comprising two Long Short Term Memory (LSTM) networks is provided for temporal analysis of R-R intervals and P wave regions in an ECG signal respectively. Output sates of the two LSTM
(Continued)

networks are merged at a dense layer along with a set of hand-crafted statistical features to create a composite feature set for classification of the AF.

10 Claims, 6 Drawing Sheets

(51) Int. Cl.
- *G16H 70/60* (2018.01)
- *G16H 50/20* (2018.01)
- *G06N 3/04* (2006.01)
- *G06N 3/08* (2006.01)
- *A61B 5/352* (2021.01)
- *A61B 5/366* (2021.01)

(52) U.S. Cl.
CPC ............ *G06N 3/0454* (2013.01); *G06N 3/08* (2013.01); *G16H 50/20* (2018.01); *G16H 70/60* (2018.01)

(58) Field of Classification Search
CPC ........ G06N 3/0454; G06N 3/08; G16H 50/20; G16H 70/60
USPC ............... 340/573.1, 439, 576; 600/518, 519
See application file for complete search history.

(56) References Cited

U.S. PATENT DOCUMENTS

| | | | |
|---|---|---|---|
| 10,213,125 B2* | 2/2019 | Cao | A61B 5/686 |
| 2003/0144597 A1* | 7/2003 | Bock | A61B 5/02405 |
| | | | 600/519 |
| 2006/0200036 A1* | 9/2006 | Kurzweil | A61B 5/746 |
| | | | 600/518 |
| 2017/0032221 A1* | 2/2017 | Wu | A61B 7/04 |
| 2019/0076031 A1* | 3/2019 | Valys | A61B 5/02405 |

OTHER PUBLICATIONS

Clifford, G.D. et al. "AF Classification from a Short Single Lead ECG Recording: the PhysioNet/Computing in Cardiology Challenge 2017," *2017 Computing in Cardiology Conference (CinC)*, Sep. 24-27, 2017, Rennes, France; pp. 1-11.

Zabihi, M. et al. "Detection of Atrial Fibrillation in ECG Hand-held Devices Using a Random Forest Classifier," *2017 Computing in Cardiology Conference (CinC)*, Sep. 24-27, 2017, Rennes, France; pp. 1-4.

Mostayed, A. et al. (2018). "Classification of 12-Lead ECG Signals with Bi-directional LSTM Network," retrieved from https://arxiv.org/ftp/arxiv/papers/1811/1811.02090.pdf. (16 pages.).

* cited by examiner

RECURRENT NEURAL NETWORK ARCHITECTURE BASED CLASSIFICATION OF ATRIAL FIBRILLATION USING SINGLE LEAD ECG

PRIORITY CLAIM

This U.S. patent application claims priority under 35 U.S.C. § 119 to: Indian Patent Application No. 201921018639, filed on 9th May, 2019. The entire contents of the aforementioned application are incorporated herein by reference.

TECHNICAL FIELD

The disclosure herein generally relates to identifying abnormal heart rhythm, and, more particularly, to systems and processor implemented methods for recurrent neural network architecture based classification of Atrial Fibrillation (AF) using single lead electrocardiogram (ECG).

BACKGROUND

Atrial Fibrillation (AF) is an electrophysiological disorder caused when abnormal electrical impulses suddenly start firing in the atria. The heart's normal rhythm goes awry, resulting in an abnormally fast heart rate with an enhanced risk of stroke and heart attack. Being one of the most common type of arrhythmias, AF is associated with significant mortality and morbidity. Presence of AF affects the electrocardiogram (ECG) morphology and is detected by cardiologists via visual inspection. However, manual detection of intermittent AF episodes from long duration ECG recordings is challenging and often impractical.

State of the art techniques of detection of AF from ECG use signal processing and machine learning techniques. Available techniques broadly belong to two categories, 1) atrial analysis based approaches and 2) ventricular response based approaches. Atrial analysis based approaches look for absence of P waves or the presence of fibrillatory f-waves in ECG, whereas ventricular response based approaches analyze irregularities in heart rate over a period of time from R-R interval distances for classification of AF. Atrial activity based approaches are known to be more accurate but they are vulnerable to background noise. Features derived from scatter plot of successive R-R intervals using Poincaré and Lorenz plots have been used in some prior art for detection of AF. Again, some prior art relies on statistical features extracted from R-R intervals to measure irregularity in heart rate caused due to AF. However, these techniques are designed for analyzing long ECG recordings.

There have been recent developments wherein classification of normal, AF and other abnormal rhythms using short (less than one minute) single lead ECG recordings have been attempted using a combination of classical and deep learning approaches. However, when single lead ECG recordings of short duration are used, accuracy of classification is a challenge.

SUMMARY

Embodiments of the present disclosure present technological improvements as solutions to one or more of the above-mentioned technical problems recognized by the inventors in conventional systems.

In an aspect, there is provided a processor implemented method for classification of atrial fibrillation (AF) comprising the steps of: acquiring, by one or more hardware processors, a single lead electrocardiogram (ECG) recorded for a first pre-defined time period being less than a minute; obtaining, by the one or more hardware processors, a first time series being an R-R interval time series based on R peaks in the acquired ECG; identifying, by the one or more hardware processors, a region having a second pre-defined time period before each of the R peaks to form a second time series, wherein the second time series is a region corresponding to P wave time series and the second pre-defined time period is in the range of 120-200 milliseconds; inputting, by the one or more hardware processors, the first time series and the second time series independently to an associated Long short-term memory (LSTM) network; merging, by the one or more hardware processors, output states of the LSTM network associated with the first time series and the second time series along with a pre-defined set of handcrafted statistical features computed from the acquired ECG to create a composite feature set for classification of the AF; and classifying the AF in the acquired ECG based on the composite feature set using a classifier.

In another aspect, there is provided a system for classification of atrial fibrillation (AF) comprising: one or more hardware processors; one or more data storage devices operatively coupled to the one or more hardware processors and configured to store instructions configured for execution by the one or more hardware processors to: acquire a single lead electrocardiogram (ECG) recorded for a first pre-defined time period being less than a minute; obtain a first time series being an R-R interval time series based on R peaks in the acquired ECG; identify a region having a second pre-defined time period before each of the R peaks to form a second time series, wherein the second time series is a region corresponding to P wave time series and the second pre-defined time period is in the range of 120-200 milliseconds; input the first time series and the second time series independently to a pair of Long short-term memory (LSTM) networks; and merge output states of the LSTM network associated with the first time series and the second time series along with a pre-defined set of handcrafted statistical features computed from the acquired ECG to create a composite feature set for classification of the AF; the pair of the LSTM networks, wherein a Bidirectional LSTM (BiLSTM) network and an LSTM network constitute the pair, and wherein the BiLSTM is configured to receive the first time series and perform a temporal analyses of the R-R intervals to capture irregular R-R intervals and the LSTM network is configured to receive the second time series and perform a temporal analyses of atrial activities, wherein the atrial activities include absence of P waves or presence of f-waves before a QRS complex in the acquired ECG; and a classifier comprising a plurality of full connected layers and a softmax function, wherein the classifier is configured to classify the AF in the acquired ECG based on the composite feature set.

In yet another aspect, there is provided a computer program product comprising a non-transitory computer readable medium having a computer readable program embodied therein, wherein the computer readable program, when executed on a computing device, causes the computing device to: acquire a single lead electrocardiogram (ECG) recorded for a first pre-defined time period being less than a minute; obtain a first time series being an R-R interval time series based on R peaks in the acquired ECG; identify a region having a second pre-defined time period before each of the R peaks to form a second time series, wherein the second time series is a region corresponding to P wave time series and the second pre-defined time period is in the range of 120-200 milliseconds; input the first time series and the second time series independently to an associated Long short-term memory (LSTM) network comprised therein; merge output states of the LSTM network associated with the first time series and the second time series along with a pre-defined set of handcrafted statistical features computed from the acquired ECG to create a composite feature set for classification of the AF; and classify the AF in the acquired ECG based on the composite feature set using a classifier comprised therein.

In accordance with an embodiment of the present disclosure, the first pre-defined time period is 33 seconds.

In accordance with an embodiment of the present disclosure, the second pre-defined time period is 200 milliseconds.

In accordance with an embodiment of the present disclosure, the region having the second pre-defined time period represents a window before a QRS complex in the acquired ECG where the P wave is located and the second time series comprises a plurality of windows on time axis.

In accordance with an embodiment of the present disclosure, the cardinality of the pre-defined set of handcrafted statistical features is 20

In accordance with an embodiment of the present disclosure, the one or more hardware processors are configured to perform a temporal analyses of the R-R intervals using a Bidirectional LSTM (BiLSTM) network to capture irregular R-R intervals; and perform a temporal analyses of atrial activities using an LSTM network, wherein the atrial activities include absence of P waves or presence off-waves before a QRS complex in the acquired ECG.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

Systems and methods of the present disclosure address an accurate classification of Atrial Fibrillation (AF) from short single lead electrocardiogram (ECG) recordings. Automatic AF detectors known in the art utilize a limited set of hand-crafted features for designing a classifier. Such AF detectors are designed based on signal processing and machine learning perspective and their outcomes may not be directly clinically interpretable or are vulnerable to noise. Morphological features are extracted from the P-Q, QRS or QT regions of the ECG for detection of AF. Since single lead ECG is used, automatic detection of P-R and P-Q intervals is often difficult, which introduces error in feature computing from those segregated intervals and compromises the performance of the classifier.

The approach provided in the present disclosure is driven by clinicians' views of detecting AF. Mimicking the perception of a clinician is achieved by using a recurrent neural network (RNN) for temporal analyses of R-R intervals and P wave regions and combining them together with a set of statistical features to obtain an improved AF classifier, in accordance with an embodiment of the present disclosure. Particularly, a Long short-term memory (LSTM) network-based approach is used that feeds a certain portion of the ECG where the P wave is most likely to be located and allows the classifier to learn the desired features for classification. Hence it is less vulnerable to noise even though single lead ECG recordings are used.

Referring now to the drawings, and more particularly to FIG. 1 through FIG. 6, where similar reference characters denote corresponding features consistently throughout the figures, there are shown preferred embodiments and these embodiments are described in the context of the following exemplary system and/or method.

Figure 1:
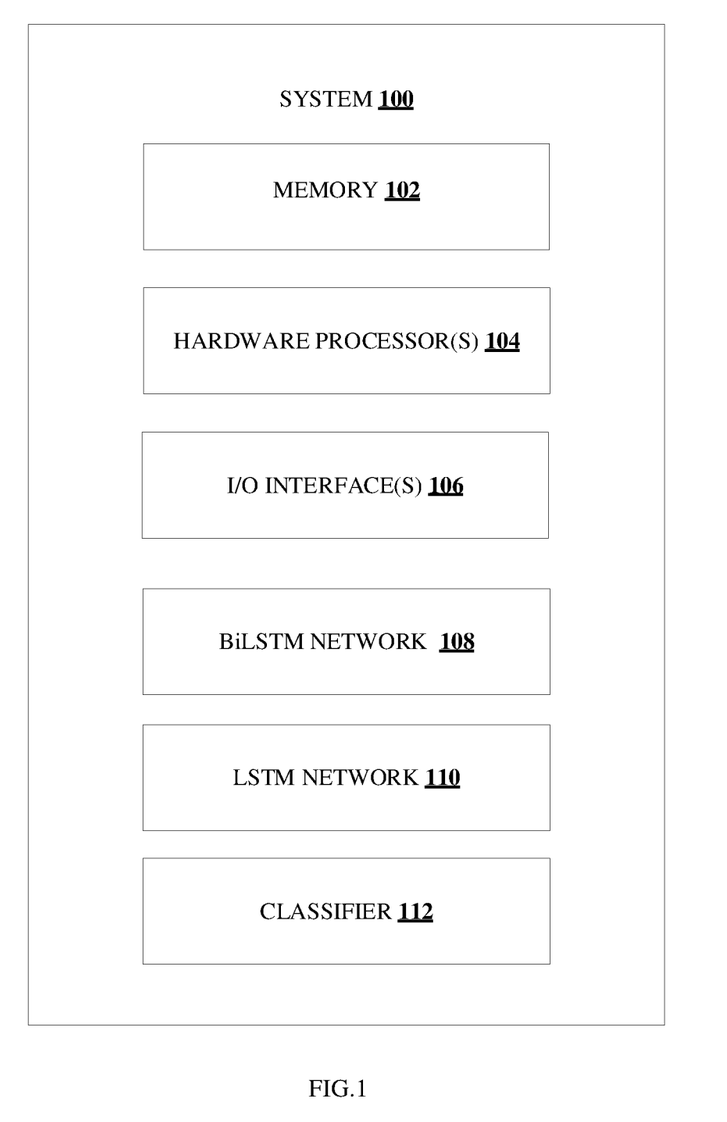
FIG. 1 illustrates an exemplary block diagram of a system for recurrent neural network architecture-based classification of atrial fibrillation using single lead electrocardiogram (ECG), in accordance with an embodiment of the present disclosure.

FIG. 1 illustrates an exemplary block diagram of a system 100 for recurrent neural network architecture based classification of atrial fibrillation using single lead electrocardiogram (ECG), in accordance with an embodiment of the present disclosure. In an embodiment, the system 100 includes one or more processors 104 being one or more hardware processors or one or more software modules or a combination thereof; communication interface device(s) or input/output (I/O) interface(s) 106; one or more data storage devices or memory 102 operatively coupled to the one or more processors 104; a pair of Long short-term memory (LSTM) networks including a Bidirectional LSTM (BiLSTM) network 108 and an LSTM network 110 described later in the description; and a classifier 112 described later in the description. The one or more processors 104 can be implemented as one or more microprocessors, microcomputers, microcontrollers, digital signal processors, central processing units, state machines, graphics controllers, logic circuitries, and/or any devices that manipulate signals based on operational instructions. Among other capabilities, the processor(s) are configured to fetch and execute computer-readable instructions stored in the memory. In the context of the present disclosure, the expressions 'processors' and 'hardware processors' may be used interchangeably. In an embodiment, the system 100 can be implemented in a variety of computing systems, such as laptop computers, notebooks, hand-held devices, workstations, mainframe computers, servers, a network cloud and the like.

The I/O interface(s) 106 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite. In an embodiment, the I/O interface(s) can include one or more ports for connecting a number of devices to one another or to another server.

The memory 102 may include any computer-readable medium known in the art including, for example, volatile memory, such as static random-access memory (SRAM) and dynamic random access memory (DRAM), and/or non-volatile memory, such as read only memory (ROM), erasable programmable ROM, flash memories, hard disks, optical disks, and magnetic tapes. In an embodiment, one or more modules (not shown) of the system 100 can be stored in the memory 102.

Figure 2:
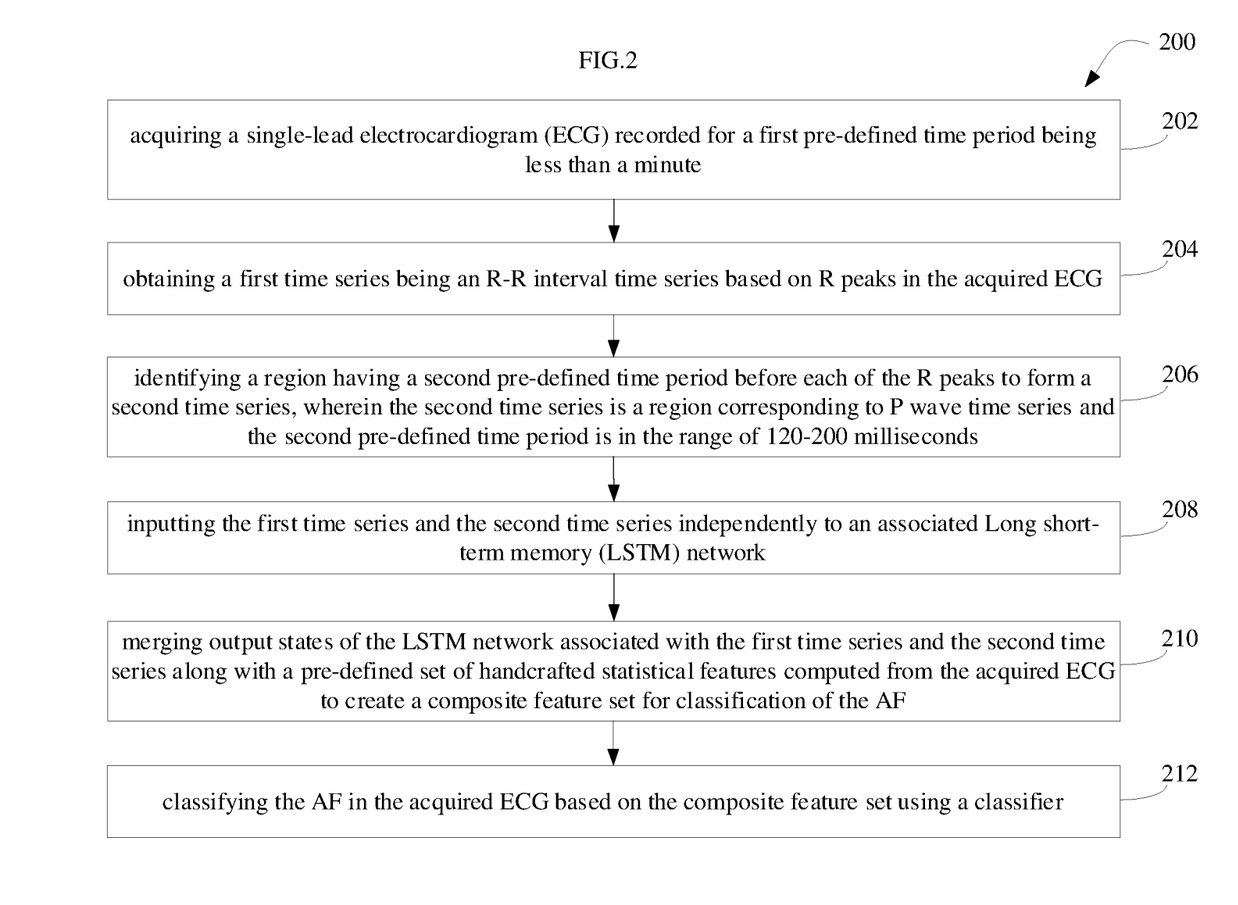
FIG. 2 illustrates an exemplary flow diagram of a computer implemented method for recurrent neural network architecture-based classification of atrial fibrillation using single lead ECG, in accordance with an embodiment of the present disclosure.

FIG. 2 illustrates an exemplary flow diagram of a computer implemented method 200 for recurrent neural network architecture-based classification of atrial fibrillation using single lead ECG, in accordance with an embodiment of the present disclosure. In an embodiment, the system 100 includes one or more data storage devices or memory 102 operatively coupled to the one or more processors 104 and is configured to store instructions configured for execution of steps of the method 200 by the one or more processors 104. The steps of the method 200 will now be explained in detail with reference to the components of the system 100 of FIG. 1. Although process steps, method steps, techniques or the like may be described in a sequential order, such processes, methods and techniques may be configured to work in alternate orders. In other words, any sequence or order of steps that may be described does not necessarily indicate a requirement that the steps be performed in that order. The steps of processes described herein may be performed in any order practical. Further, some steps may be performed simultaneously.

Figure 3A:
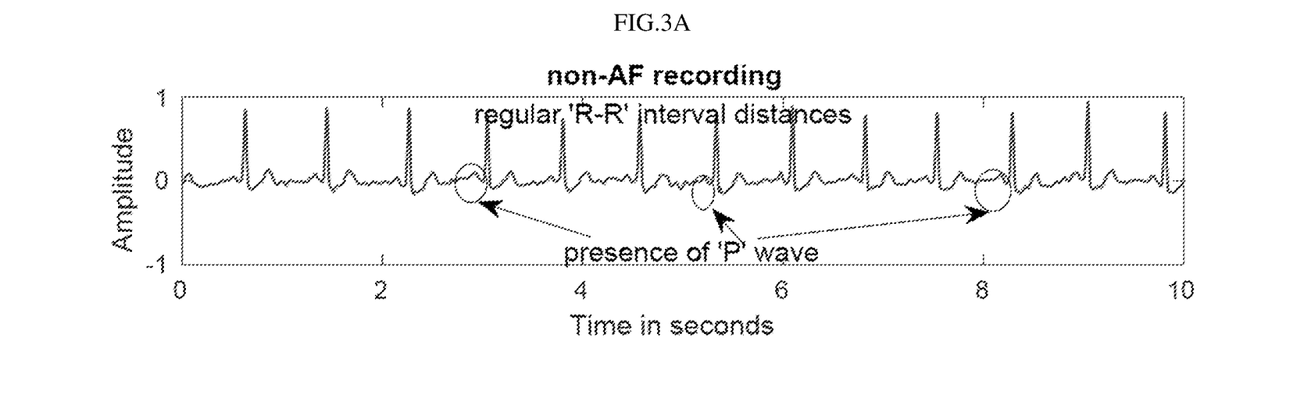
FIG. 3A and FIG. 3B illustrate an exemplary non-Atrial Fibrillation (AF) and AF ECG waveform respectively, as known in the art.
Figure 3B:
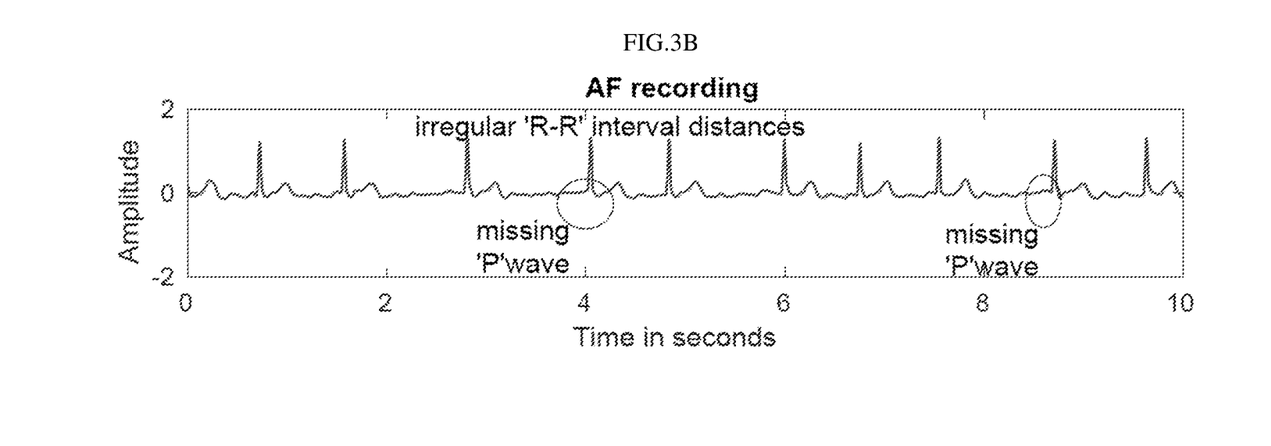

FIG. 3A and FIG. 3B illustrate an exemplary non-Atrial Fibrillation (AF) and AF ECG waveform respectively, as known in the art. Clinicians look for two important markers in ECG for AF, viz., (i) absence of P waves or presence of f-waves before the QRS complex, and (ii) irregularly irregular R-R intervals. The method 200 of the present disclosure is designed to capture both these markers based on temporal analyses of the ECG.

Figure 4:
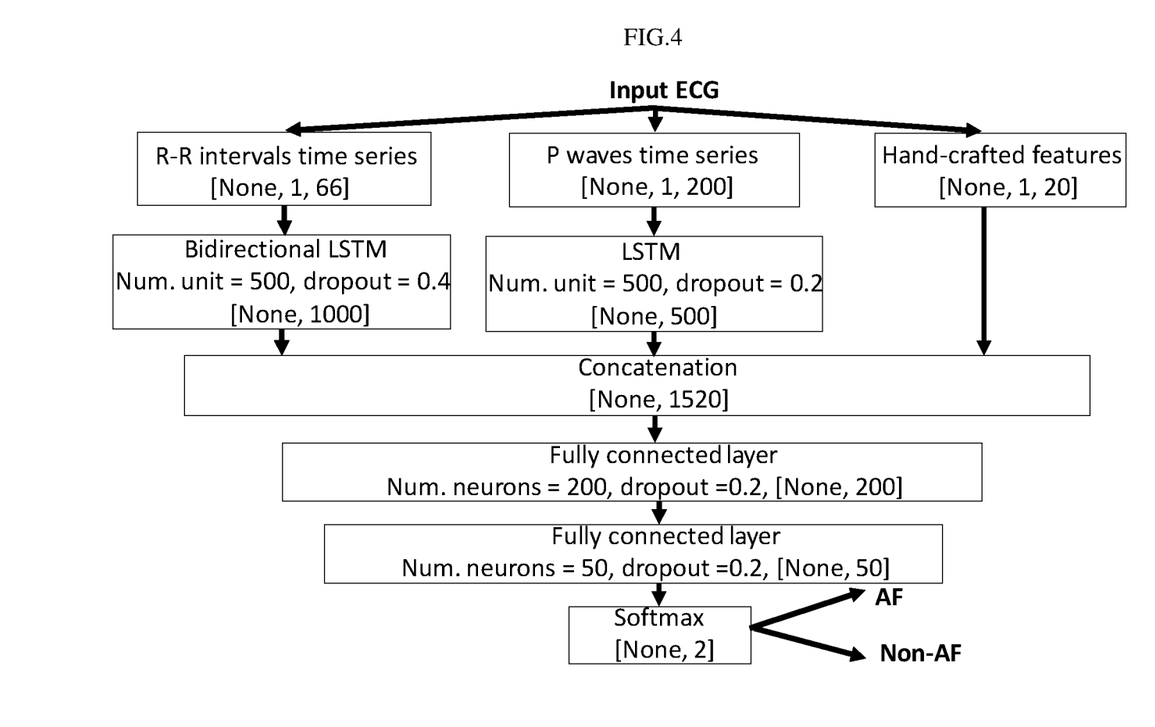
FIG. 4 illustrates a network architecture for classifying AF, in accordance with an embodiment of the present disclosure.

FIG. 4 illustrates a network architecture along with its tensor dimensions at output of different layers for classifying AF, in accordance with an embodiment of the present disclosure. For instance, in the block R-R intervals times series with dimension [None, 1, 66], None indicates no predefined training size, 1 is the dimension of the time series and 66 represents the number of time samples. In sequence models, RNNs use their internal memory to process a sequence of input time series for extraction of temporal patterns that can be used for classification or prediction. LSTM is a class of RNN that can effectively learn a longer pattern of unknown length as it can deal with the exploding and vanishing gradient problems faced by RNNs during training. LSTM does this because of its cell structure that enables deleting less important information from memory. For an input sequence $x_t=\{x_1, \ldots x_T\}$, an LSTM cell with one forget gate computes a hidden vector sequence $h_t=\{h_1, \ldots h_T\}$ by iterating the following equations over t.

$$f_t = \sigma(W_{xf}x_t + W_{hf}h_{t-1} + b_f) \quad \rightarrow (1)$$

$$i_t = \sigma(W_{xi}x_t + W_{hi}h_{t-1} + b_i) \quad \rightarrow (2)$$

$$c_t = f_t * c_{t-1} + i_t * \tan h(W_{xc}x_t + W_{hc}h_{t-1} + b_c) \quad \rightarrow (3)$$

$$o_t = \sigma(W_{xo}x_t + W_{ho}h_{t-1} + b_o) \quad \rightarrow (4)$$

$$h_t = o_t * \tan h(c_t) \quad \rightarrow (5)$$

Here, σ represents the logistic sigmoid function, * denotes element-wise product operation. Input gate, forget gate, output gate and cell activation vectors are represented by i, f, o and c respectively. Hyperbolic tangent tan h is used as the input activation function.

In accordance with an embodiment of the present disclosure, the one or more processors 104 are configured to acquire, at step 202, a single lead electrocardiogram (ECG) recorded for a first pre-defined time period being less than a minute. Further at step 204, a first time series is obtained, wherein the first time series is an R-R interval time series based on R peaks in the acquired ECG. In an embodiment, the open source implementation of Behar's algorithm maybe used for extraction of R peaks to construct the R-R interval time series. In an embodiment, irregular sampling rate of the time series is fixed to 2 Hertz (Hz) using cubic-spline interpolation technique and mapped to the range of 0 to 1. In an embodiment, the first pre-defined time period or the duration of ECG recording is 33 seconds as explained later in the description with reference to the experimental dataset.

Since atrial activities behave chaotically during AF, P waves are either not present or there are f-waves in ECG. Although detection of such activities makes an AF classifier more accurate, automatic segmentation of P waves using signal processing approaches is a difficult task due to the varying morphology of P waves. In accordance with the present disclosure, temporal analyses of the atrial activities is performed using the LSTM network 110. The input sequence to the LSTM network 110 is formed by considering a window before the QRS complex in the ECG where the P wave is typically located and stacking multiple such windows on time axis. Accordingly, in an embodiment, the one or more processors 104 are configured, at step 206, to identify a region having a second pre-defined time period before each of the R peaks to form a second time series such that the second time series is a region corresponding to P wave time series. In accordance with the present disclosure, the region having the second pre-defined time period represents a window before a QRS complex in the acquired ECG where the P wave is located and the second time series comprises a plurality of windows on the time axis. Typically, duration of PR interval distance lies between 120-200 milliseconds. Accordingly, in the present disclosure, the second pre-defined time period, is in the range of 120-200 milliseconds. Particularly, in an embodiment, the second pre-defined time period may be 200 milliseconds and it ends 33 milliseconds before a reference R peak.

Rapid irregular fluctuation in heart rate is a known symptom of AF. This directly reflects in the ECG, as the R peaks do not repeat after a fixed interval. Clinicians are trained to identify such irregularities via visual inspection. In accordance with the present disclosure, long term temporal dependencies in R-R intervals in an ECG recording are modeled using the BiLSTM network. Both previous and future context of a time series can be effectively utilized in the BiLSTM network, as it processes the input sequence in both forward and backward direction. In accordance with an embodiment of the present disclosure, the one or more processors 104 are configured to input, at step 208, the first time series and the second time series independently to a pair of Long short-term memory (LSTM) networks. In an embodiment, the pair of the LSTM networks include the BiLSTM network 108 and the LSTM network 110. In an embodiment, the BiLSTM network 108 is configured to receive the first time series from step 204 and perform a temporal analyses of the R-R intervals to capture irregular R-R intervals while the LSTM network 110 is configured to receive the second time series from step 206 and perform a temporal analyses of atrial activities, wherein the atrial activities include absence of P waves or presence of f-waves before the QRS complex in the acquired ECG.

In accordance with an embodiment of the present disclosure, the one or more processors 104 are configured to merge, at step 210, output states of the LSTM network associated with the first time series and the second time series along with a pre-defined set of handcrafted statistical features computed from the acquired ECG to create a composite feature set for classification of the AF.

In an embodiment, 20 handcrafted statistical features are considered to measure the heart rate variability. For instance, entropy related features are used to measure the randomness of a time series. For a time series $RR_t=\{RR_1, RR_2, \ldots RR_m\}$, approximate entropy $ApEn(RR_t, q, r)$ is measured in terms of a predefined pattern length (q) and a similarity criterion parameter r. A sequence of vectors $\{x_q(1), x_q(2), \ldots x_q(m-q+1)\}$ in real q-dimensional space is defined from $RR_t$, such that $x_q(i)=\{RR_i, RR_{i+1}, RR_{i+2} \ldots RR_{i+q-1}\}$. Two such vectors $x_q(i)$ and $x_q(j)$ are similar if $|RR_{i+k}-RR_{j+k}|<r$ for $0<k<q$. Let $C_{iq}(r)=$(number of $x_q(j)$ similar to $x_q(i))/(m-q+1)$. If $C_{iq}(r)$ indicates the mean of all $C_{iq}(r)$ for $i \in 1 \ldots m-q+1$, then ApEn is defined as:

$$ApEn(RR_t, q, r) = \ln\left[\frac{C_q(r)}{C_{q+1}(r)}\right] \quad (6)$$

Sample entropy $(SampEn(RR_t, q, r)$ is defined as:

$$(SampEn(RR_t, q, r) = -\ln\left[\frac{A}{B}\right] \quad (7)$$

Here, A=number of vector pairs where $|x_{q+1}(i)-x_{q+1}(j)|<r$
B=number of vector pairs where $|x_q(i)-x_q(j)|<r$,
Shannon entropy of $RR_t$ is calculated as:

$$E_{sh} = -\sum_{b=1}^{N} pr_b \log pr_b \quad (8)$$

A normalized histogram of N bins is created from $RR_t$. Empirical probability of $b^{th}$ histogram bin is denoted by $pr_b$. Here $b \in 1 \ldots N$ and $\Sigma_{b=1}^{N} pr_b = 1$. In accordance with an embodiment of the present disclosure, the remaining features include statistical parameters like mean, variance, maximum, minimum, range, kurtosis, skewness of $RR_t$, pNN20, pNN50, Poincaré and Lorenz plot features.

In accordance with an embodiment of the present disclosure, the one or more processors 104 are configured to classify, at step 212, the AF in the acquired ECG based on the composite feature set using a classifier. In an embodiment, the classifier 112 comprises a plurality of full connected layers and a softmax function. Typically, the classifier 112 may be a Support Vector Machine (SVM). As shown in FIG. 4, in an embodiment, output states of the two LSTM networks are merged at the dense layer along with the hand-crafted statistical features and passed through two fully connected layers and softmax layer for classification.

Experimental Data

The PhysioNet challenge 2017 dataset comprising a total of 8528 single lead ECG recordings was used. As per available annotation, 5154 recordings of the dataset are normal sinus rhythms, 771 are AF, 2557 are non-AF but abnormal rhythms and remaining 46 recordings are noisy. However, detail disease information of the 2557 non-AF rhythms are not provided. Since the methods of the present disclosure are specifically designed for classifying AF, the dataset for binary classification was re-labeled by grouping all non-AF recordings into a single class. Thus the modified dataset contains 771 AF and 7757 non-AF (5154+2557+46=7757) recordings. This makes the dataset quite imbalanced with a ratio of majority (non-AF) to minority (AF) class close to 10:1. The signals were sampled at 300 Hz, and bandpass filtered with cut off frequencies of 0.5 Hz and 40 Hz during recording. The entire dataset was partitioned into three portions based on random selection, maintaining the skewness of the original dataset in all of them. 60% of the total dataset was selected for training, 20% for internal validation and the remaining 20% was initially kept hidden for testing. The training and validation set were exclusively used for optimization of different network parameters empirically and creation of training models. Once the training model was finalized, the evaluation was performed on the hidden set.

Figure 5:
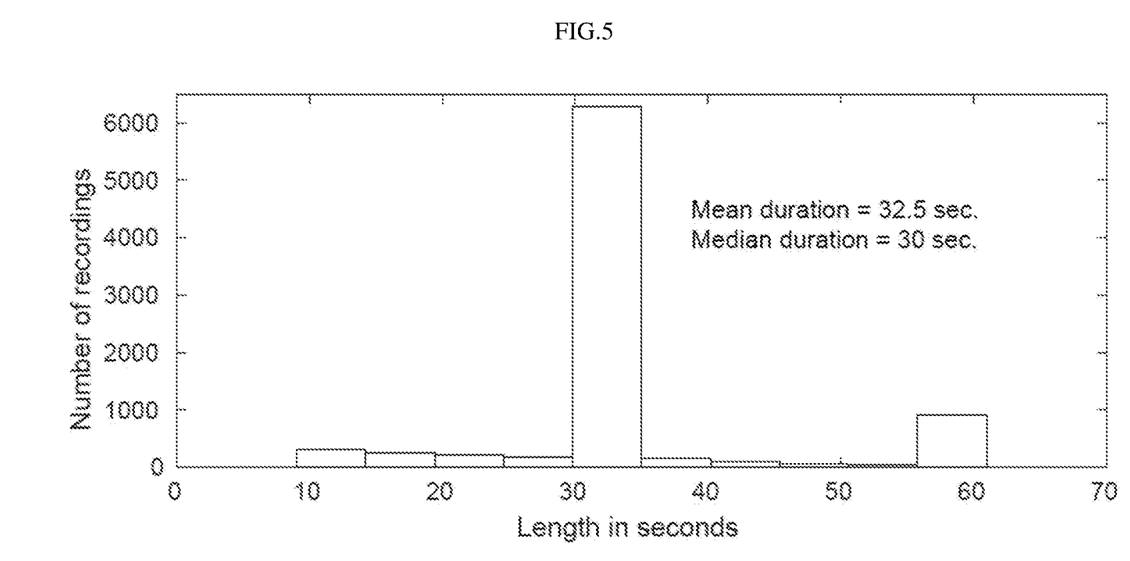
FIG. 5 illustrates a histogram of data length in the PhysioNet 2017 dataset available in the public domain.

Duration of the recordings in PhysioNet dataset varies from 9 seconds to 61 seconds. Theoretically, a longer input sequence ensures a better learning. However, an LSTM structure requires all its input sequences of same time length. FIG. 5 illustrates a histogram of data length in the PhysioNet 2017 dataset available in the public domain. It may be noted that most of the recordings in the dataset have a duration close to 30 seconds with a mean duration of 32.5 seconds. Hence, the duration of ECG for analyzing R-R intervals (the first pre-defined time period) was selected as 33 seconds. The input sequence to the BiLSTM network contains 66 data points, due to its pre-defined sampling rate of 2 Hz. For a shorter recording, it was repeated from beginning to achieve the desired length.

For the analyses of P wave regions, 10 consecutive cardiac cycles were selected from a random location in ECG to construct the input sequence to the LSTM network. This duration was selected based on the shortest available recording in the dataset so that the original signal morphology can be used without appending. This also supports the perception of the clinicians, as 10 consecutive cycles with no P waves or presence of f-waves can be marked as an AF event. The handcrafted features were calculated from the entire data, as these are not dependent on the duration of recordings. Drop-out was applied in the LSTM layers and the fully connected layers to mitigate the chance of over-fitting. The neurons of the fully connected layers were activated using Rectified Linear Unit (ReLU) function. Initial weights of the fully connected and softmax layers were set using Xavier initialization. In this procedure, initial weights of the neurons in a layer were assigned from a Gaussian distribution of zero mean and a finite variance $$\mathrm{var} = \frac{2}{n_{in} + n_{out}},$$

where $n_{in}$ and $n_{out}$ represent the number of input and output neurons. The cross-entropy loss was minimized during training using Adam optimizer with 100 epochs, mini-batch size of 50 and learning rate of 0.001. The minority class was assigned 10 times more class-weight than the majority class in order to overcome the class imbalance problem in the dataset. Hence the gradient computed from the instances of the majority class becomes 10 times larger than the majority class, paying more attention to AF.

Figure 6:
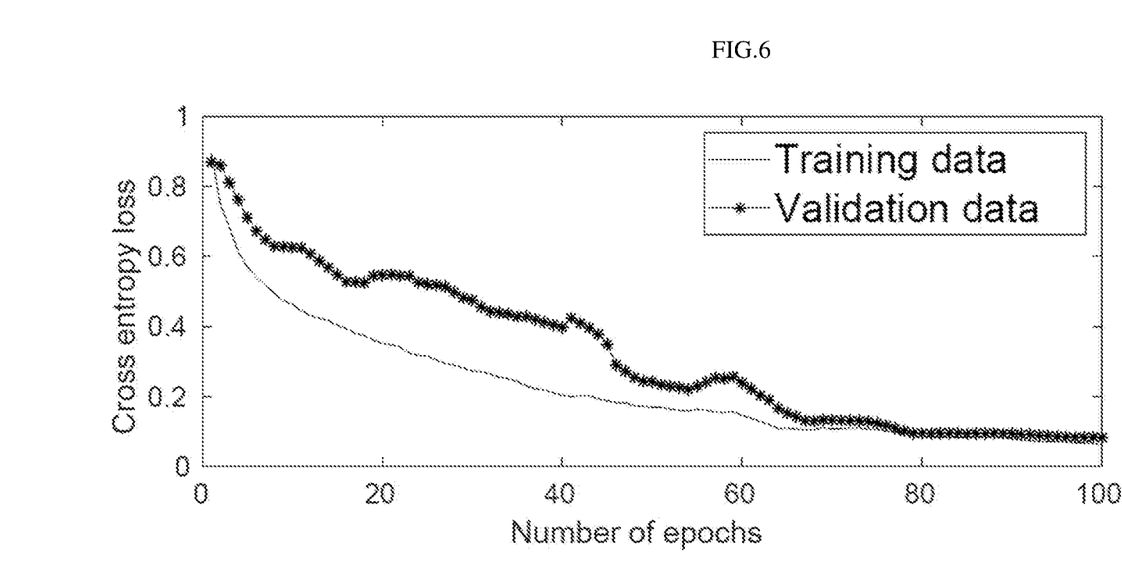
FIG. 6 illustrates cross entropy loss at different epochs on training and validation data, in accordance with an embodiment of the present disclosure.

FIG. 6 illustrates cross entropy loss at different epochs on training and validation data, in accordance with an embodiment of the present disclosure. It may be noted that the loss on both the training and the validation data gets minimized and starts saturating after 80 epochs. The final training model was created using 100 epochs.

Experimental Results

Performance of a method in an embodiment of the present disclosure is reported in terms of sensitivity and specificity of detecting AF. Table 1 below shows the classification performance obtained by individual input components (i.e. R-R intervals sequence, P wave regions and handcrafted features) along with the performance improvement achieved by the method in an embodiment of the present disclosure that merges the input components at the dense layer.

TABLE 1

Performance analyses on the validation and the test dataset.

| Network Structure | Validation set | | Test set | |
|---|---|---|---|---|
| | $S_e$ | $S_p$ | $S_e$ | $S_p$ |
| R-R intervals sequence → BiLSTM → fully connected layers → softmax | 0.86 | 0.97 | 0.83 | 0.97 |
| P wave regions → LSTM → fully connected layers → softmax | 0.74 | 0.93 | 0.71 | 0.91 |
| Handcrafted 20 features → fully connected layers → softmax | 0.83 | 0.95 | 0.82 | 0.96 |
| Method of the present disclosure, merging all three inputs | 0.93 | 0.98 | 0.92 | 0.98 |

The classifiers based on R-R intervals and the handcrafted features yield promising accuracy scores individually. However, the sensitivity needs to be improved to realize an accurate AF detector. As known in the art, irregular heart rate variability is a well-known marker for AF. However, such irregularities are often associated with a number of cardiac conditions other than AF. Hence the overall sensitivity gets reduced due to a large number of false negative cases produced by the classifiers. Table 1 shows that a major performance improvement is achieved by the method of the present disclosure, which significantly improves the sensitivity on both validation and test set without affecting the specificity.

The method, in an embodiment of the present disclosure, was compared with top four joint winning entries in the PhysioNet challenge 2017 as shown in Table 2 below. The submitted entries were ranked by the challenge organizers based on mean F1-score of classifying normal, AF and other abnormal rhythms. Since the method of the present disclosure is designed to classify AF and non-AF rhythms, F1-scores of detecting AF was considered here for performance comparison.

TABLE 2

Comparison with prior art approaches

| Authors | Methodology used | F-1 score of AF |
|---|---|---|
| Teijeiro et al. | Combination of RNN and XGBoost | 0.85 |
| Datta et al. | Domain specific features followed by cascaded binary classifier | 0.80 |
| Zabihi et al. | 150 features in time, frequency and time-frequency domain are fed to a random forest classifier | 0.79 |
| Hong et al. | Ensemble of DNN and domain specific features | 0.85 |
| Method of the present disclosure | Concatenated LSTM | 0.87 |

Table 2 shows that the method of the present disclosure outperforms the top scoring entries in the PhysioNet challenge in AF detection. Considering the actual annotation of the dataset, the method of the present disclosure yields F1-scores of 0.94, 0.87 and 0.72 respectively in detecting normal, AF and other rhythms on the test set. Mean F1 score of detecting the three class labels was calculated as 0.843, which is comparable to the previously reported accuracies on the dataset. The method of the present disclosure performs better than the reported accuracy scores in detecting normal and AF. However, the performance was suboptimal in detecting other abnormal rhythms, as the method of the present disclosure is specifically designed for AF classification. It may be noted that the experiment was conducted on the publicly available portion of the PhysioNet challenge.

Thus, in accordance with the present disclosure, accurate classification of AF from single-lead ECG is achieved using the network architecture of FIG. 4, wherein temporal analyses of R-R intervals and P wave regions using LSTM networks is performed and the output states are merged with a set of handcrafted features related to heart rate variability. The step 210 of merging is integrated into the practical application of classifying the AF in the acquired ECG using the steps 202 through 208 of the method 200 described above.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:

1. A processor implemented method for classification of atrial fibrillation (AF), the method comprising the steps of:
   acquiring, by one or more hardware processors, a single lead electrocardiogram (ECG) recorded for a first pre-defined time period being less than a minute;
   obtaining, by the one or more hardware processors, a first time series being an R-R interval time series based on R peaks in the acquired ECG;
   identifying, by the one or more hardware processors, a region having a second pre-defined time period before each of the R peaks to form a second time series, wherein the second time series is a region corresponding to P wave time series and the second pre-defined time period is in the range of 120-200 milliseconds;
   inputting, by the one or more hardware processors, the first time series and the second time series independently to a pair of Long short-term memory (LSTM) networks, wherein a Bidirectional LSTM (BiLSTM) network and an LSTM network constitute the pair, and wherein the step of inputting the first time series and the second time series independently to the pair of LSTM networks is followed by:
      performing a temporal analyses of the R-R intervals using the BiLSTM network to capture irregular R-R intervals; and
      performing a temporal analyses of atrial activities using the LSTM network, wherein the atrial activities include absence of P waves or presence of f-waves before a QRS complex in the acquired ECG;
   merging, by the one or more hardware processors, output states of the LSTM network associated with the first time series and the second time series along with a pre-defined set of handcrafted statistical features computed from the acquired ECG to create a composite feature set for classification of the AF; and
   classifying the AF in the acquired ECG based on the composite feature set using a classifier.

2. The processor implemented method of claim 1, wherein the first pre-defined time period is 33 seconds.

3. The processor implemented method of claim 1, wherein the second pre-defined time period is 200 milliseconds.

4. The processor implemented method of claim 1, wherein the region having the second pre-defined time period represents a window before the QRS complex in the acquired ECG where the P wave is located and the second time series comprises a plurality of windows on time axis.

5. The processor implemented method of claim 1, wherein the cardinality of the pre-defined set of handcrafted statistical features is 20.

6. A system for classification of atrial fibrillation, the system comprising:
one or more hardware processors;
one or more data storage devices operatively coupled to the one or more hardware processors and configured to store instructions configured for execution by the one or more hardware processors to:
acquire a single lead electrocardiogram (ECG) recorded for a first pre-defined time period being less than a minute;
obtain a first time series being an R-R interval time series based on R peaks in the acquired ECG;
identify a region having a second pre-defined time period before each of the R peaks to form a second time series, wherein the second time series is a region corresponding to P wave time series and the second pre-defined time period is in the range of 120-200 milliseconds;
input the first time series and the second time series independently to a pair of Long short-term memory (LSTM) networks; and
merge output states of the LSTM network associated with the first time series and the second time series along with a pre-defined set of handcrafted statistical features computed from the acquired ECG to create a composite feature set for classification of the AF;
the pair of the LSTM networks, wherein a Bidirectional LSTM (BiLSTM) network and an LSTM network constitute the pair, and wherein the BiLSTM is configured to receive the first time series and perform a temporal analyses of the R-R intervals to capture irregular R-R intervals and the LSTM network is configured to receive the second time series and perform a temporal analyses of atrial activities, wherein the atrial activities include absence of P waves or presence of f-waves before a QRS complex in the acquired ECG; and
a classifier comprising a plurality of full connected layers and a softmax function, wherein the classifier is configured to classify the AF in the acquired ECG based on the composite feature set.

7. The system of claim 6, wherein the first pre-defined time period is 33 seconds.

8. The system of claim 6, wherein the second pre-defined time period is 200 milliseconds.

9. The system of claim 6, wherein the region having the second pre-defined time period represents a window before a QRS complex in the acquired ECG where the P wave is located and the second time series comprises a plurality of windows on time axis.

10. A computer program product comprising a non-transitory computer readable medium having a computer readable program embodied therein, wherein the computer readable program, when executed on a computing device, causes the computing device to:
acquire a single lead electrocardiogram (ECG) recorded for a first pre-defined time period being less than a minute;
obtain a first time series being an R-R interval time series based on R peaks in the acquired ECG;
identify a region having a second pre-defined time period before each of the R peaks to form a second time series, wherein the second time series is a region corresponding to P wave time series and the second pre-defined time period is in the range of 120-200 milliseconds;
input the first time series and the second time series independently to a pair of Long short-term memory (LSTM) networks, wherein a Bidirectional LSTM (BiLSTM) network and an LSTM network constitute the pair, and wherein the step of inputting the first time series and the second time series independently to the pair of LSTM networks is followed by:
performing a temporal analyses of the R-R intervals using the BiLSTM network to capture irregular R-R intervals; and
performing a temporal analyses of atrial activities using the LSTM network, wherein the atrial activities include absence of P waves or presence of f-waves before a QRS complex in the acquired ECG;
merge output states of the LSTM network associated with the first time series and the second time series along with a pre-defined set of handcrafted statistical features computed from the acquired ECG to create a composite feature set for classification of the AF; and
classify the AF in the acquired ECG based on the composite feature set using a classifier.

* * * * *